(12) United States Patent
Lee

(10) Patent No.: US 10,576,030 B2
(45) Date of Patent: Mar. 3, 2020

(54) HAIR-DYEING COMPOSITION FOR MINIMIZING HAIR DAMAGE AND SCALP IRRITATION CAUSED BY APPLYING AMMONIA AND METHOD OF PRODUCING THE SAME

(71) Applicant: AreumDawoon Cosmetics Co., Ltd., Cheonan-si, Chungcheongnam-do (KR)

(72) Inventor: Jae Il Lee, Cheonan-si (KR)

(73) Assignee: AREUMDAWOON COSMETICS CO., LTD., Cheonan-si, Chungcheongnam-do (KR)

( * ) Notice: Subject to any disclaimer, the term of this patent is extended or adjusted under 35 U.S.C. 154(b) by 211 days.

(21) Appl. No.: 15/621,575

(22) Filed: Jun. 13, 2017

(65) Prior Publication Data
US 2018/0064617 A1 Mar. 8, 2018

(30) Foreign Application Priority Data
Sep. 2, 2016 (KR) .......................... 10-2016-0113128

(51) Int. Cl.
| | | |
|---|---|---|
| *A61K 8/34* | (2006.01) |
| *A61K 8/22* | (2006.01) |
| *A61K 8/31* | (2006.01) |
| *A61K 8/02* | (2006.01) |
| *A61K 8/19* | (2006.01) |
| *A61K 8/41* | (2006.01) |
| *A61K 8/86* | (2006.01) |
| *A61K 8/97* | (2017.01) |
| *A61K 8/98* | (2006.01) |
| *A61Q 5/10* | (2006.01) |

(52) U.S. Cl.
CPC .............. *A61K 8/34* (2013.01); *A61K 8/0291* (2013.01); *A61K 8/19* (2013.01); *A61K 8/22* (2013.01); *A61K 8/31* (2013.01); *A61K 8/342* (2013.01); *A61K 8/41* (2013.01); *A61K 8/86* (2013.01); *A61K 8/97* (2013.01); *A61K 8/986* (2013.01); *A61Q 5/10* (2013.01); *A61K 2800/75* (2013.01); *A61K 2800/805* (2013.01)

(58) Field of Classification Search
None
See application file for complete search history.

(56) References Cited

FOREIGN PATENT DOCUMENTS

| KR | 10-0358490 B1 | 10/2002 |
|---|---|---|
| KR | 10-0725650 B1 | 6/2007 |
| KR | 10-0927103 B1 | 11/2009 |
| KR | 10-1005316 B1 | 1/2011 |

*Primary Examiner* — Robert A Wax
*Assistant Examiner* — Randeep Singh
(74) *Attorney, Agent, or Firm* — Rabin & Berdo, P.C.

(57) ABSTRACT

A hair-dyeing composition that minimizes hair damage and scalp irritation caused by applying ammonia to the scalp and that reduces the ammonia odor peculiar to hair-dyeing compositions is provided. The hair-dyeing composition additionally supplements the hair with amino acids similar to hair proteins to decrease hair damage, especially hair roughness and hair shortening, for healthy dyeing. A method of producing the hair-dyeing composition is additionally provided and includes melting, mixing, and emulsifying steps.

5 Claims, 8 Drawing Sheets

HAIR-DYEING COMPOSITION FOR MINIMIZING HAIR DAMAGE AND SCALP IRRITATION CAUSED BY APPLYING AMMONIA AND METHOD OF PRODUCING THE SAME

BACKGROUND OF THE INVENTION

Field of the Invention

The present invention relates to a hair-dyeing composition with an effect of minimizing hair damage and scalp irritation caused by ammonia prescription and ammonia odor and a method of producing the same. In particular, it relates to a hair-dyeing composition with an effect of minimizing hair damage and scalp irritation caused by ammonia prescription and ammonia odor, which is capable of decreasing ammonia odor peculiar to a hair-dyeing composition and also of supplementing the hair with amino acids similar to hair proteins to decrease hair damage, especially hair roughness and hair shortening, for healthy dyeing and a method of producing the same.

Description of the Related Art

Generally, oxidized permanent hair dyeing compositions can be used for covering a gray hair, styling a gray hair, and styling a hair. Most of them consist of a first agent and a second agent and they are mixed each other immediately before use. The first agent includes a diamine-based oxidation dyeing, an ammonia water, a monoethanolamine, an ammonium thioglycolate etc. and the second agent includes a hydrogen peroxide and the like.

The components are essential ingredients of the hair dyeing composition and are also causative materials of causing a hair damage (hair loss, hair cutting, hair cracking), a stimulation of the scalp (erythema, swelling, itching, stinging, rash and the like), and a specific smell.

For example, the ammonia water, which is used as an alkaline agent, serves to swell and softens the hair, so that the oxidation dye can be easily penetrated into the hair and become solid, thereby increasing the durability of the hair dyeing. However, due to toxicity and strong volatility thereof, it is also a substance capable of causing a stimulation of respiratory organs and seborrheic dermatitis.

In order to decrease these various side effects, if the content of the alkaline agent, especially the ammonia water is decreased, the hair dying strength, which is a basic characteristic of the hair dyeing composition, is lowered.

Korean Patent Laid-Open Publication No. 2001-0075811 discloses "a neutral hair dyeing agent composition" and a hair dyeing composition capable of dyeing at a neutral pH by containing sodium silicate, which minimizes a damage of hair and preserves the dyed colors for a long time during dyeing hair by using the neutral hair dyeing agent. To this end, the neutral hair dyeing agent composition contains 0.05 to 5.0% by weight of sodium silicate based on the total weight of the composition and is hair-dyed at a neutral (pH 6.5 to 7.0).

Korean Patent Laid-Open Publication No. 2006-0129874 discloses "a henna and aloe-containing composition for dyeing and bleaching hair" and compositions capable of additionally containing the henna and the aloe in the conventional synthetic hair dyeing or bleaching agents. Also, it is disclosed that the scalp damage and the irritating smell production can be remarkably reduced and the heat generation is suppressed, thereby providing comfortability to the person to be treated.

Korean Patent Laid-Open Publication No. 2009-0085765 discloses "a composition of hair coloring product containing charcoal powder" having effects capable of remarkably reducing generation of odor adsorption and irritating odor during the dyeing process and preventing the hair from being damaged owing to the synergistic action of urea and isopropyl myristate by mixing the composition of hair coloring product containing charcoal powder with the hair coloring product including a first agent and a second agent.

SUMMARY OF THE INVENTION

The present invention has been made in an effort to solve the problems of the conceptual description of the conventional art as described above, and the objective of the present invention is to provide a hair-dyeing composition with an effect of minimizing hair damage and scalp irritation caused by ammonia prescription and ammonia odor, which is capable of decreasing ammonia odor peculiar to a hair-dyeing composition and also of supplementing the hair with amino acids similar to hair proteins to decrease hair damage, especially hair roughness and hair shortening, for healthy dyeing and a method of producing the same.

The present invention provides a hair-dyeing composition which is particularly capable of decreasing ammonia odor and a method of producing the same. It has also been found that the above problem can be solved by using menthol of an essential oil to enhance the deodorizing effect and containing a coffee extract component, a milk extract component, and an amino acid component of soybeans more in the hair-dyeing composition to alleviate irritation and damage of the hair and scalp, thereby completing the present invention.

According to an aspect of the invention to achieve the objects described above, there is provided a hair-dyeing composition including: a first agent; and a second agent, wherein the first agent includes: a base material containing polyoxyethylene octyl ether phosphate and polyoxyethylene oleyl ether phosphate as essential components and additionally an auxiliary component selected from the group consisting of cetearyl alcohol, behenyl alcohol, mineral oil, and any mixture of two or more of these at from 5 to 30% by weight; an alkalizing agent selected from the group consisting of monoethanolamine, ammonia water (concentration: 28% by weight), and any mixture of these at from 5 to 25% by weight; a color developer at from 0.01 to 2% by weight; and a solvent as the remainder, and the second agent includes: a base material selected from the group consisting of polyoxyethylene oleyl ether phosphate, cetearyl alcohol, and any mixture of these at from 1 to 10% by weight; an oxidizing agent at from 12 to 20% by weight; a pH adjusting agent at from 0.1 to 1% by weight; and a solvent as the remainder.

Preferably, the first agent contains a deodorant at from 0.01 to 0.5% by weight.

Preferably, the deodorant is L-menthol.

Preferably, the first agent further contains a hair protecting and scalp irritation alleviating agent selected from the group consisting of a coffee extract, a milk extract, a soybean extract, and any mixture of two or more thereof at from 0.1 to 10% by weight based on the total weight of the first agent.

Preferably, in the hair protecting and scalp irritation alleviating agent, the mixing ratio of coffee extract: milk extract: soybean extract is 2:1:3 as a weight ratio.

According to an aspect of the invention to achieve the objects described above, there is provided a method of producing a hair-dyeing composition including a first agent production step and a second agent production step, in which the first agent includes: a base material containing polyoxyethylene octyl ether phosphate and polyoxyethylene oleyl ether phosphate as essential components and additionally an auxiliary component selected from the group consisting of cetearyl alcohol, behenyl alcohol, mineral oil, and any mixture of two or more of these at from 5 to 30% by weight; an alkalizing agent selected from the group consisting of monoethanolamine, ammonia water (concentration: 28% by weight), and any mixture of these at from 5 to 25% by weight; a color developer at from 0.01 to 2% by weight; and a solvent as the remainder, and the second agent includes: a base material selected from the group consisting of polyoxyethylene oleyl ether phosphate, cetearyl alcohol, and any mixture of these at from 1 to 10% by weight; an oxidizing agent at from 12 to 20% by weight; a pH adjusting agent at from 0.1 to 1% by weight; and a solvent as the remainder, wherein the first agent production step includes: (1) a first melting step in which a solvent and a color developer are put in a tank and melted by being heated at a temperature in a range of from 70 to 90° C.; (2) a mixing step in which a base material is melted by being heated at a temperature in a range of from 70 to 90° C. and then put in the tank; (3) a first emulsification step in which the mixture obtained in the mixing step is emulsified; (4) a first cooling step in which the first product acquired in the first emulsification step is cooled to a temperature in a range of from 50 to 55° C.; (5) a second emulsification step in which an alkalizing agent is added to the cooled first product and emulsified; and (6) a second cooling step in which the second product acquired in the second emulsification step is cooled to a temperature in a range of from 35 to 40° C.

Preferably, the first agent production step further comprises a third emulsification step of further mixing a deodorant and emulsifying after the second emulsification step.

Preferably, in the third emulsification step, the deodorant is L-menthol.

Preferably, the first agent production step further comprises a fourth emulsification step of further mixing and emulsifying a hair protecting and scalp irritation alleviating agent after the third emulsification step.

Preferably, the first agent production step further includes a fifth emulsification step of further mixing an additive selected from the group consisting of a first additive selected from the group consisting of an antioxidant, a sequestering agent, a perfume, and any mixture of two or more thereof; a second additive selected from the group consisting of a hair softening agent, a conditioning agent, a hair polishing agent, and any mixture of two or more thereof; a third additive selected from the group consisting of a sequestering agent, a perfume, and any mixture of two or more thereof and emulsifying after the fourth emulsification step.

Preferably, after only ammonia water is added and emulsified in the second emulsification step, the alkalizing agent other than ammonia water is added and emulsified in the third emulsification step.

Preferably, the emulsification is performed by physically stirring the mixture at from 3000 to 4000 rpm for a time in a range of from 3 to 30 minutes by using a homomixer.

Preferably, the emulsification is performed so that the stirring time gradually decreases as the order increases.

Preferably, the second agent production step includes: (1) a melting step in which a solvent, an oxidizing agent, and a pH adjusting agent of aqueous components are put in a tank and melted by being heated at a temperature in a range of from 70 to 90° C.; (2) a mixing step in which a base material is melted by being heated at a temperature in a range of from 70 to 90° C. and then put in the tank; and (3) an emulsification step in which the mixture obtained in the mixing step is emulsified.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENT

Hereinafter, preferred embodiments of the invention will be described in more detail with reference to the accompanying drawings.

The hair-dyeing composition according to the present invention contains a first agent and a second agent, in which the first agent contains a base material selected from the group consisting of cetearyl alcohol, behenyl alcohol, polyoxyethylene octyl ether phosphate, polyoxyethylene oleyl ether phosphate, mineral or a mixture of two of more of these at from 5 to 30% by weight, an alkalizing agent selected from the group consisting of monoethanolamine, ammonia water (concentration: 28% by weight), or any mixture of these at from 5 to 25% by weight, a color developer at from 0.01 to 2% by weight, and a solvent as the remainder and the second agent contains a base material selected from the group consisting of polyoxyethylene oleyl ether phosphate, cetearyl alcohol, or any mixture of these at from 1 to 10% by weight, an oxidizing agent at from 12 to 20% by weight, a pH adjusting agent at from 0.1 to 1% by weight, and a solvent as the remainder.

The present inventors have studied a method of decreasing the irritating odor, especially ammonia odor, generated when using an oxidative hair-dyeing composition and confirmed that spherical micelles or bar-shaped micelles formed in the emulsified state of a general hair-dyeing composition cannot decrease the ammonia odor. As a result of studies on various emulsification methods, the present inventors have confirmed that the ammonia odor is decreased when ammonia water is enclosed in a micelle formed to have a layered structure, thereby completing the present invention.

Figure 1:
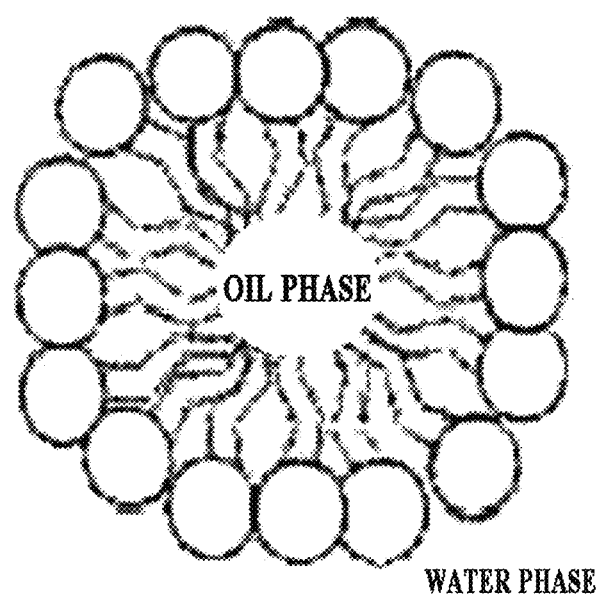
FIG. 1 is a diagram illustrating schematically a shape of spherical micelles.

In detail, a general emulsion is in an O/W (oil-in-water) form and forms mostly a spherical or bar-shaped micelle. Hence, the micelles of conventional hair-dyeing compositions also form the same spherical or bar-shaped micelles. Since the ammonia water contained in the water phase of the hair-dyeing composition is present on the outside (water phase) rather than the inside of the micelle, the ammonia water volatilizes and causes an irritating odor to adversely affect the bodies of the practitioner and the customer during the procedure of dyeing (see FIG. 1).

Figure 2:
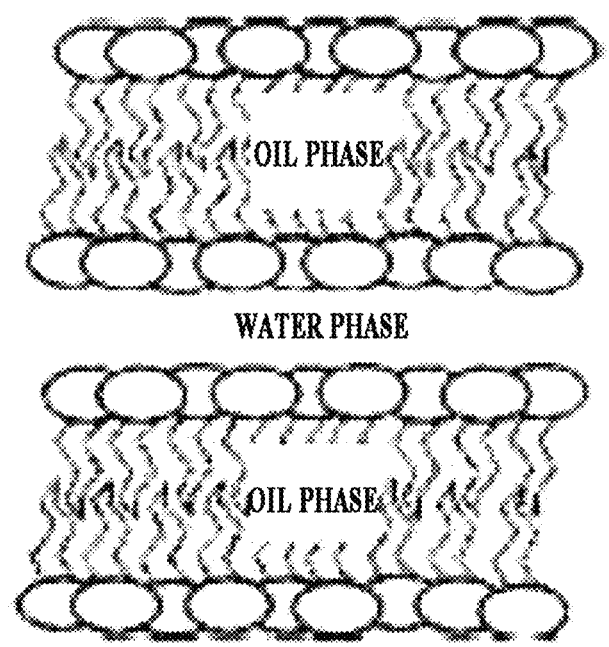
FIG. 2 is a diagram illustrating schematically a shape of micelles having a layered structure.

Accordingly, it has been confirmed that the volatilization of ammonia water is not prevented by a general emulsification method, and various emulsification experiments have been thus conducted. As a result, it has been confirmed that the volatilization is prevented by enclosing ammonia water in a micelle formed to have a layered structure (see FIG. 2).

Figure 3:
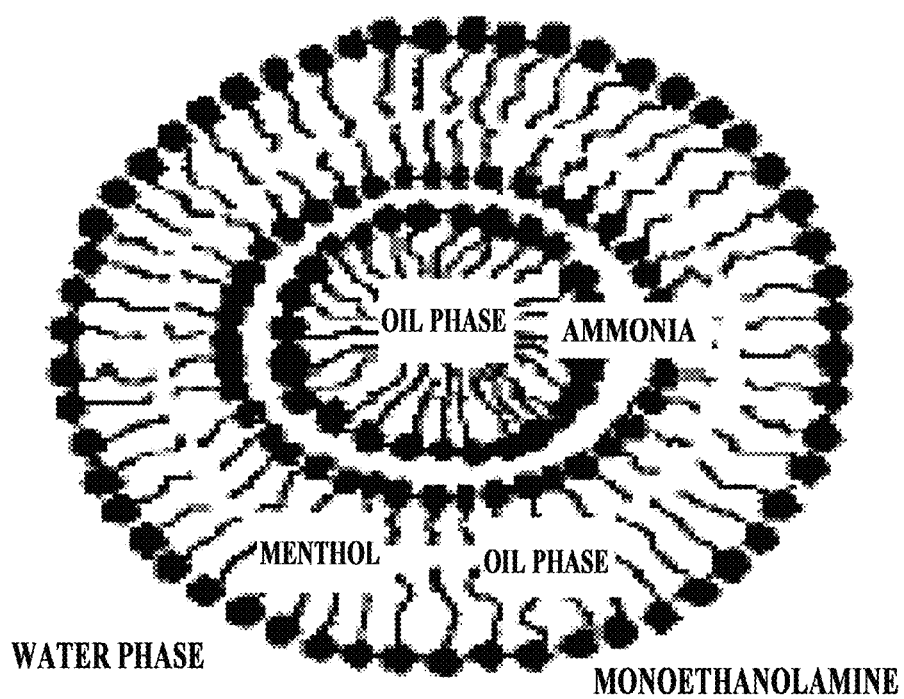
FIG. 3 is a diagram illustrating schematically a shape of micelles obtained through an emulsification by using a polyoxyethylene alkyl ether phosphate-based substance according to the present invention.

As a result of various experiments, it has been confirmed that a polyoxyethylene alkyl ether phosphate-based substance is suitable as a substance which forms a stable layer structure by a general emulsification method, and it has also been confirmed that a combination of polyoxyethylene octyl ether phosphate and polyoxyethylene oleyl ether phosphate is suitable for the enclosure of ammonia water (see FIG. 3).

FIG. 3 illustrates a layered micelle structure emulsified using a combination of polyoxyethylene octyl ether phosphate and polyoxyethylene oleyl ether phosphate as a polyoxyethylene alkyl phosphate, and it has been confirmed that ammonia water is enclosed in between a layer and another layer to decrease the ammonia odor.

The base material of the first agent preferably contains polyoxyethylene octyl ether phosphate and polyoxyethylene oleyl ether phosphate as essential components and may additionally contain an auxiliary component selected from the group consisting of cetearyl alcohol, behenyl alcohol, mineral oil, and any mixture of two or more thereof. The mineral oil is a by-product produced in the course of refining crude oil, contains alkanes and paraffin as main components, is a relatively inexpensive substance and produced in a significantly large quantity, and can be commercially purchased and used by those skilled in the art.

In the first agent, the base material may be contained in an amount of from 5 to 30% by weight based on the total weight of the first agent, but when the content is out of the above range, there may be a problem that the odor decreasing effect is insufficient as the shape of the micelle is not properly maintained and the time dependent stability (thinning) changes.

In the first agent, the alkalizing agent may be contained in an amount of from 5 to 25% by weight based on the total weight of the first agent, but when the content is out of the above range, there may be a problem that the hair-dyeing power is insufficient, hair damage is severe, scalp is excessively irritated, and the odor peculiar to an alkalizing agent is stronger.

The color developer in the first agent may be preferably selected from the group consisting of toluene-2,5-diamine sulfate, 2,4-diaminophenoxyethanol hydrochloride, m-aminophenol, resorcinol, and any mixture of two or more thereof, but these are exemplary of the present invention, and the invention is not intended to be limited thereto. The color developer may be contained in an amount of from 0.01 to 2% by weight based on the total weight of the first agent, but when the content is out of the above range, there may be a problem that proper color development is not achieved.

In the first agent, the solvent may be water.

The first agent may further contain a deodorant at from 0.01 to 0.5% by weight based on the total weight of the first agent, and the deodorant may be L-menthol. L-menthol as a deodorant is the main component of peppermint oil and a white crystal obtained by distilling, cooling, and purifying the foliage of peppermint. It provides a unique refreshing scent and refreshing feeling and has a relaxing effect and a function of alleviating pain or itching. It is fragrant and has a cool taste, and thus it is used as stomachic and medicinal stuffs for neuralgia and tuberculosis, and oral fragrance, and the plaster thereof is used for rheumatism and neuralgia. It is represented by a chemical formula of $C_{10}H_{20}O$, is an opaque crystal, and has a molecular weight of 156.27 g/mol, a melting point of 42° C., and a boiling point of 212° C. By the addition of such a deodorant, the effect of deodorizing the hair-dyeing composition is enhanced and especially the effect of decreasing secondary ammonia odor has been confirmed. When the amount of L-menthol used as the deodorant is out of the above range, there may be a problem that the function of deodorization is weak and the formulation is destabilized (separated).

The first agent may further contain a hair protecting and scalp irritation alleviating agent selected from the group consisting of a coffee extract, a milk extract, a soybean extract, and any mixture of two or more thereof at from 0.1 to 10% by weight based on the total weight of the first agent. In the hair protecting and scalp irritation alleviating agent, the mixing ratio of coffee extract:milk extract:soybean extract may be 2:1:3 as a weight ratio. It has been confirmed that an effect of alleviating the scalp irritation due to dyeing and an effect of restoring the damaged hair are achieved by the use of such a hair protecting and scalp irritation alleviating agent. There may be a problem that the effect of alleviating the scalp irritation and the function of restoring the damaged hair are insufficient when the content is out of the above range and the compatibility of the hair protecting and scalp irritation alleviating agent with the raw material components is poor when the content is excessive.

The coffee extract in the hair protecting and scalp irritation alleviating agent is preferably Arabica that is native to Ethiopia and grows in Brazil, Colombia, Costa Rica, and the like. It has a production quantity of 70% and mainly grows at a temperature of from 15 to 24° C., a humidity of 60%, and an altitude of from 600 to 2000 m. It has a flat oval shape and a turquoise color and is characterized by a rich flavor and a sour taste. Examples of the efficacy thereof may include antimicrobial activity, an antioxidative effect, the improvement of inflammation, the improvement of blood circulation, skin elasticity, the promotion of metabolism, the elimination of waste products, and a fat decomposing effect. As the chemical components constituting Arabica, there are beta sitosterol, caffeolol, caffein, caffetanic acid, campesterol, chlorogenic acid, linoleic acid, oleic acid, palmitic acid, and stearic acid. The extract (cold brewed coffee extract) can be obtained by a cold extraction method in order to maximize the efficacy of these components. The cold extraction method can be carried out by keeping the coffee beans immersed in water so that the active components in the coffee are eluted. The purification to remove impurities through centrifugation or filtration may be further performed. After purification, concentration under reduced pressure or freeze-drying may be further performed. The coffee extract extracted by such a cold extraction method can be acquired as an ethanol fraction through reflux extraction with ethanol. The amount of water used, the temperature for cold immersion, and the time for cold immersion in the cold extraction are not particularly limited, but the amount of water used may be preferably in a range of from 50 to 150 g of coffee bean per 1 L of water. There may be a problem that the yield of coffee extract decreases and the productivity thus decreases when the amount of coffee beans is too small based on the amount of water used and the extraction efficiency decreases when the amount of coffee beans is too great. The temperature for cold immersion may be preferably in a range of from room temperature to 45° C. There may be a problem that the consumption of unnecessary energy, particularly energy for cooling or heating increases when the temperature is lower than room temperature or higher than 45° C. The time for cold immersion may be preferably in a range of from 1 to 3 days. There may be a problem that the extraction efficiency decreases when the time for cold immersion is too short and the productivity decreases when the time for cold immersion is too long. The ethanol fraction is acquired by adding ethanol to the coffee extract acquired by cold extraction of coffee so as to obtain an aqueous ethanol solution having a final concentration of from 50 to 90% (v/v) and performing reflux extraction for from 3 to 7 hours. The reflux extraction may be repeated from 1 to 5 times and preferably from 2 to 4 times. After reflux extraction and purification by filtration or the like, concentration under reduced pressure or freeze-drying may be further performed.

Milk extract has been used as a secret of beauty from the ancient Egypt and is a source of essential amino acids that the body needs. The main component of milk is protein, and casein (amino acid) accounts for 80% thereof. In terms of efficacy, it promotes collagen synthesis of fibroblasts, promotes cell growth of fibroblasts and keratinocytes, and thus has a function of improving wrinkle by this. As the amino acids constituting the milk extract, essential amino acids such as glycine, alanine, serine, threonine, valine, leucine, phenylalanine, tyrosine, proline, methionine, cystine, cysteic acid, aspartic acid, glutamic acid, arginine, histidine, and lysine and hydrophilic amino acids are the main components, and they exhibit favorable hair protecting and scalp irritation alleviating effect. The milk extract used in the present invention specifically refers to hydrolyzed milk protein, and this is obtained by hydrolyzing casein (casein K) obtained from milk with renin of an enzyme to isolate and purify the glycoprotein.

The main components of the soybean extract are isoflavones, saponins, and phospholipids, and isoflavones are also called phytoestrogens since they play a role similar to estrogen of the female hormone. It has been reported to inhibit the enzymatic action involved in cancer cell proliferation and to be effective in the treatment of various diseases and the skin aesthetics for postmenopausal women. Saponin is a functional substance which lowers blood cholesterol, inhibits the formation of peroxidized lipids that are constantly produced in cells, and is known to help prevent aging and senile dementia including atherosclerosis. Lecithin, a main component of phospholipids, is a constituent of various biofilms such as cell membranes in living organisms. The main function thereof is moisturizing, antioxidant, and anti-inflammatory actions for the skin. The soybean extract used in the present invention refers to hydrolyzed soy protein, which is obtained by dispersing defatted soybeans in water, adjusting the pH with an alkali, adding trypsin which is one kind of proteolytic enzymes to hydrolyze the protein, then inactivating the enzyme by a heat treatment, then cooling, filtering, and purifying the resultant, and then adjusting the pH to from 4.0 to 4.5 with an acid.

The hair protecting and scalp irritation alleviating effect is exhibited when the hair protecting and scalp irritation alleviating agent contains the extract selected from the group consisting of mixtures of a coffee extract, a milk extract, and a soybean extract having a ratio of 2:1:3 at from 0.1 to 10% by weight.

The base material and solvent of the second agent may be the same and/or similar to the base material and solvent of the first agent.

The oxidizing agent of the second agent may be hydrogen peroxide (concentration: 35% by weight). There may be a problem that the hair-dyeing power decreases when the amount of the second agent used is insufficient and side effects such as hair damage and scalp irritation increase when the oxidizing agent is used too much.

The pH adjusting agent of the second agent may be selected from the group consisting of tetrasodium pyrophosphate, phosphoric acid, and any mixture thereof. The pH adjusting agent may be added in an amount appropriate to control the pH of the composition to be acquired. It is preferable to adjust the pH of the entire composition in a range of from 2.5 to 3.5.

The first agent may further contain a first additive selected from the group consisting of an antioxidant, a sequestering agent, a perfume, and any mixture of two or more thereof.

The first agent may further contain a second additive selected from the group consisting of a hair softening agent, a conditioning agent, a hair polishing agent, and any mixture of two or more thereof.

The second agent may further contain a third additive selected from the group consisting of a sequestering agent, a perfume, and any mixture thereof.

The above-mentioned first to third additives may be commercially purchased by those skilled in the field of hairstyling, particularly in the hair-dyeing composition manufacturing field and contained in the composition in an appropriate amount to control the physical properties of the hair-dyeing composition and to improve the stability and the like of the product.

In addition, the method of producing a hair-dyeing composition according to the present invention includes a first agent production step and a second agent production step, in which the first agent contains a base material selected from the group consisting of cetearyl alcohol, behenyl alcohol, polyoxyethylene octyl ether phosphate and polyoxyethylene oleyl ether phosphate, mineral oil, and any mixture of two or more thereof at from 5 to 30% by weight, an alkalizing agent selected from the group consisting of monoethanolamine, ammonia water (concentration: 28% by weight), and any mixture thereof at from 5 to 25% by weight, a color developer at from 0.01 to 2% by weight, and a solvent as the remainder and the second agent contains a base material selected from the group consisting of polyoxyethylene oleyl ether phosphate, cetearyl alcohol, and any mixture thereof at from 1 to 10% by weight, an oxidizing agent at from 12 to 20% by weight, a pH adjusting agent at from 0.1 to 1% by weight, and a solvent as the remainder. Here, the first agent production step includes (1) a first melting step in which a solvent and a color developer of aqueous components are put in a tank and melted by being heated at a temperature in a range of from 70 to 90° C.; (2) a mixing step in which a base material of an oily component is melted by being heated at a temperature in a range of from 70 to 90° C. and then put in the tank; (3) a first emulsification step in which the mixture obtained in the mixing step is emulsified; (4) a first cooling step in which the first product acquired in the first emulsification step is cooled to a temperature in a range of from 50 to 55° C.; (5) a second emulsification step in which an alkalizing agent is added to the cooled first product and emulsified; and (6) a second cooling step in which the second product acquired in the second emulsification step is cooled to a temperature in a range of from 35 to 40° C.

In the first melting step of the first agent production step, a solvent and a color developer of aqueous components are put in a tank and melted by being heated at a temperature in a range of from 70 to 90° C. When the melting temperature is lower than 70° C. in the melting step, there may be a problem that the melting is insufficient and the shape of the micelles is not uniform. When the melting temperature is higher than 90° C., the inherent structures of the raw materials are affected to cause a specific odor and browning.

In the mixing step of the first agent production step, a base material of an oily component is melted by being heated at a temperature in a range of from 70 to 90° C. and then put in the tank.

In the first emulsification step of the first agent production step, the mixture obtained in the mixing step is emulsified. The emulsification may be performed by physically stirring the mixture at from 3000 to 4000 rpm for a time in a range of from 3 to 30 minutes by using a homomixer. In particular, the emulsification in this step may be preferably performed by stirring the components in the tank at from 3000 to 4000 rpm for from 20 to 30 minutes by using a homomixer. There may be a problem that the phase of the emulsion to be acquired is ununiform and the time course of the emulsion is affected, that is, separation or thinning of the emulsion is caused when the stirring speed in this first emulsification step is slower than 3000 rpm and the stirring time is shorter than 20 minutes. When the stirring speed in this first emulsification step is faster than 4000 rpm and the stirring time is longer than 30 minutes, there may be a problem that excessive bubbles are generated and the composition to be acquired changes black as the oxygen contained in the bubbles promotes the oxidation of the dye.

In the first cooling step of the first agent production step, the first product acquired in the first emulsification step is cooled to a temperature in a range of from 50 to 55° C.

In the second emulsification step of the first agent production step, an alkalizing agent is added to the cooled first product and emulsified. The emulsification is preferably performed by stirring and emulsifying the mixture at from 3000 to 4000 rpm for from 5 to 10 minutes by using a homomixer. In the cooling step after the first emulsification, the alkalizing agent, particularly ammonia water, is added in order to enclose the alkalizing agent, particularly ammonia water, in the water phase of the layered micelle. There may be a problem that it is difficult to enclose the alkalizing agent, particularly ammonia water, and the low odor property is thus not improved when the stirring speed and the stirring time are out of the above ranges.

In the second cooling step of the first agent production step, the second product acquired in the second emulsification step is cooled to a temperature in a range of from 35 to 40° C.

The base material of the first agent preferably contains polyoxyethylene octyl ether phosphate and polyoxyethylene oleyl ether phosphate as essential components and may additionally contain an auxiliary component selected from the group consisting of cetearyl alcohol, behenyl alcohol, mineral oil, and any mixture of two or more thereof.

A third emulsification step of further mixing a deodorant and emulsifying may be further included after the second emulsification step. The emulsification in the third emulsification step may also be performed by adding a deodorant to the product acquired after the second emulsification step and stirring and emulsifying the mixture at from 3000 to 4000 rpm for from 5 to 10 minutes by using a homomixer. In this step, the deodorant is added in order to enclose the deodorant, preferably L-menthol, in the oily layer of the layered micelles. When the stirring speed and the stirring time are out of the above range, it is difficult to enclose the deodorant, preferably L-menthol.

A fourth emulsification step of further mixing and emulsifying a hair protecting and scalp irritation alleviating agent may be further included after the third emulsification step. This step is particularly preferably carried out by physical stirring at 25° C. or higher and 3000 rpm or more. There may be a problem that the components are not uniformly mixed in the phase when the emulsification is performed at a temperature lower than or equal to the above temperature and a stirring speed slower than or equal to the above stirring speed. There may be a problem of bubble generation and the change of inherent structure, discoloration, the change of odor, and phase change of the raw materials due to temperature when the temperature is higher than 30° C. and the stirring speed is faster than 4000 rpm.

A fifth emulsification step of further mixing an additive selected from the group consisting of a first additive, a second additive, a third additive, and any mixture of two or more thereof and emulsifying may be further included after the fourth emulsification step.

In a case in which the first agent contains ammonia water and an alkalizing agent other than ammonia water as the alkalizing agent, only ammonia water may be added and emulsified in the second emulsification step and the alkalizing agent other than ammonia water may be then added and emulsified in the third emulsification step. Consequently, the addition of deodorant may be performed by enclosing a deodorant, preferably L-menthol, in the oily layer of the layered micelles and then enclosing an alkaline agent other than ammonia water, for example monoethanolamine, in the water phase. By positioning ammonia water particularly having a strong odor inside the micelle through such sequential enclosure, it is possible to greatly decrease ammonia odor and to improve the low odor property of the whole hair-dyeing composition.

The emulsification may be performed so that the stirring time gradually decreases as the order increases, that is, the stirring time of the first emulsification step is the longest, and the stirring time is shorter in the second emulsification step, and the stirring time is the shortest in the third emulsification step. This is because in order to gradually enclose other components in the micelle after the micelle is once formed.

The method of producing a hair-dyeing composition according to the present invention may further include a second agent production step. Here, the second agent production step includes (1) a melting step in which a solvent, an oxidizing agent, and a pH adjusting agent of aqueous components are put in a tank and melted by being heated at a temperature in a range of from 70 to 90° C.; (2) a mixing step in which a base material of an oily component is melted by being heated at a temperature in a range of from 70 to 90° C. and then put in the tank; and (3) an emulsification step in which the mixture obtained in the mixing step is emulsified. In other words, the second agent production step includes (1) a melting step, (2) a mixing step, and (3) an emulsifying step.

In the melting step of (1), the aqueous components among the components constituting the second agent which contains a base material selected from the group consisting of polyoxyethylene oleyl ether phosphate, cetearyl alcohol, and any mixture thereof at from 1 to 10% by weight, an oxidizing agent at from 12 to 20% by weight, a pH adjusting agent at from 0.1 to 1% by weight, and a solvent as the remainder are put in a main tank and melted by being heated at a temperature in a range of from 70 to 90° C. There may be a problem that the melting is insufficient when the melting temperature is lower than 70° C. in the melting step. When the melting temperature is higher than 90° C., the inherent structures of the raw materials are affected to cause a specific odor and browning of the composition to be acquired.

In the mixing step of (2), separately from the melting step, the oily components among the components constituting the second agent are melted by being heated at a temperature in a range of from 70 to 90° C. and then put in the main tank. There may be a problem that the melting is insufficient when the melting temperature is lower than 70° C. in the melting step. when the melting temperature is higher than 90° C., the inherent structures of the raw materials are affected to cause a specific odor and browning.

The emulsification step of (3) includes an emulsification step in which the components in the main tank are stirred and emulsified at from 3000 to 4000 rpm for from 5 to 10 minutes by using a homomixer. There may be a problem that the phase of the emulsion to be acquired is ununiform and the time course of the emulsion is affected, that is, separation or thinning of the emulsion is caused when the stirring speed in this emulsification step is slower than 3000 rpm and the stirring time is shorter than 5 minutes. There may be a problem that excessive bubbles are generated and a desired viscosity is not obtained when the stirring speed is faster than 4000 rpm and the stirring time is longer than 10 minutes.

The second agent production step may further include an oxidizing agent mixing step in which the mixture emulsified in the emulsification step of (3) is cooled to from 25 to 30° C. and an oxidizing agent is added to and mixed with the emulsified mixture after the emulsification step (3). There may be a problem that the oxidizing agent is not uniformly mixed with the emulsified mixture when the temperature at the time of adding the oxidizing agent is lower than the above range. There may be a problem that the content of the oxidizing agent is insufficient due to evaporation of the oxidizing agent and insufficient dyeing is caused when the temperature is higher than the above range.

Hereinafter, preferred Examples and Comparative Examples of the present invention will be described.

The following Examples are illustrative of the present invention and should not be construed as limiting the scope of the invention.

EXAMPLES 1 TO 11 AND COMPARATIVE EXAMPLE 1

The first agent and the second agent in the hair-dyeing composition according to the present invention were produced by using the components presented in the following Table 1 (prescription for the production of the first agent) and Table 2 (prescription for the production of the second agent) and determining the order of addition.

Coffee extract, milk extract, and soybean extract used in the following description are acquired by cold extraction, and the cold extraction may be performed as follows, for example, in the case of a coffee extract. The *Arabica* coffee beans are immersed in purified water to be 100 g/L. Extraction is performed at 37° C. for 2 days by using a 5 L tank. After extraction, the extract is centrifuged to remove impurities. The coffee extract is refluxed 3 times, each for 5 hours, by adding ethanol so as to finally obtain a 70% (v/v) aqueous ethanol solution, cold-settled, and then filtered through 3 μm, 1 μm, and 0.25 μm filter paper by using a filtering device. When the filtration is completed, the extract obtained in the extraction step is transferred to the concentration tank and concentrated under reduced pressure or freeze-dried at 60° C. or lower. A mixed extract is produced by using purified water and a butylene glycol solvent so that the freeze-dried extract thus obtained is contained at from 1.0 to 10% by weight.

Milk extract and the soybean extract are also produced by carrying out the same and/or similar process as that for the coffee extract described above.

TABLE 1

| Function | Parts | Comparative Example 1 | Example 1 | Example 2 | Example 3 | Example 4 | Example 5 |
|---|---|---|---|---|---|---|---|
| Solvent | W | Remainder | Remainder | Remainder | Remainder | Remainder | Remainder |
| Sequestering agent | W | 0.1 | 0.1 | 0.1 | 0.1 | 0.1 | 0.1 |
| Antioxidant 1 | W | 0.2 | 0.2 | 0.2 | 0.2 | 0.2 | 0.2 |
| Antioxidant 2 | W | 0.5 | 0.5 | 0.5 | 0.5 | 0.5 | 0.5 |
| Color developer 1 | W | 0.1 | 0.1 | 0.1 | 0.1 | 0.1 | 0.1 |
| Color developer 2 | W | 0.05 | 0.05 | 0.05 | 0.05 | 0.05 | 0.05 |
| Color developer 3 | W | 0.015 | 0.015 | 0.015 | 0.015 | 0.015 | 0.015 |
| Color developer 4 | W | 0.05 | 0.05 | 0.05 | 0.05 | 0.05 | 0.05 |
| Base material 1 | O | 8.0 | | 8.0 | 8.0 | 8.0 | 8.0 |
| Base material 2 | O | 2.0 | | 2.0 | 2.0 | 2.0 | 2.0 |
| Base material 3 | O | | 2.0 | 2.0 | | — | 2.0 |
| Base material 4 | O | | 4.0 | 4.0 | | — | 4.0 |
| Base material 5 | O | | | | 6.0 | — | |
| Base material 6 | O | | | | | 6.0 | |
| Base material 7 | O | | | | | — | 2.0 |
| Base material 8 | O | | 2.0 | 2.0 | 2.0 | 2.0 | 2.0 |
| Alkalizing agent 1 | W | 9.0 | 9.0 | 9.0 | 9.0 | 9.0 | 9.0 |
| Alkalizing agent 2 | W | 6.0 | 6.0 | 6.0 | 6.0 | 6.0 | 6.0 |
| Deodorant | O | | 0.1 | 0.1 | 0.1 | 0.1 | 0.1 |
| Perfume | O | 0.5 | 0.5 | 0.5 | 0.5 | 0.5 | 0.5 |
| Protecting and alleviating agent 1 | W | | 2.0 | 2.0 | 2.0 | 2.0 | 2.0 |
| Protecting and alleviating agent 2 | W | | 1.0 | 1.0 | 1.0 | 1.0 | 1.0 |
| Protecting and alleviating agent 3 | W | | 3.0 | 3.0 | 3.0 | 3.0 | 3.0 |

TABLE 1-continued

|  | Example | | | | | |
|---|---|---|---|---|---|---|
| Function | 6 | 7 | 8 | 9 | 10 | 11 |
| Solvent | Remainder | Remainder | Remainder | Remainder | Remainder | Remainder |
| Sequestering agent | 0.1 | 0.1 | 0.1 | 0.1 | 0.1 | 0.1 |
| Antioxidant 1 | 0.2 | 0.2 | 0.2 | 0.2 | 0.2 | 0.2 |
| Antioxidant 2 | 0.5 | 0.5 | 0.5 | 0.5 | 0.5 | 0.5 |
| Color developer 1 | 0.1 | 0.1 | 0.1 | 0.1 | 0.1 | 0.1 |
| Color developer 2 | 0.05 | 0.05 | 0.05 | 0.05 | 0.05 | 0.05 |
| Color developer 3 | 0.015 | 0.015 | 0.015 | 0.015 | 0.015 | 0.015 |
| Color developer 4 | 0.05 | 0.05 | 0.05 | 0.05 | 0.05 | 0.05 |
| Base material 1 | 8.0 | 8.0 | 8.0 | 8.0 | 8.0 | 8.0 |
| Base material 2 | 2.0 | 2.0 | 2.0 | 2.0 | 2.0 | 2.0 |
| Base material 3 | 4.0 | 2.0 | 2.0 | 2.0 | 2.0 | 2.0 |
| Base material 4 | 2.0 | 4.0 | 4.0 | 4.0 | 4.0 | 4.0 |
| Base material 5 | | | | | | |
| Base material 6 | | | | | | |
| Base material 7 | | | | | | |
| Base material 8 | 2.0 | 2.0 | 2.0 | 2.0 | 2.0 | 2.0 |
| Alkalizing agent 1 | 9.0 | 9.0 | 9.0 (1) | 9.0 (2) | 9.0 (3) | 9.0 (1) |
| Alkalizing agent 2 | 6.0 | 6.0 | 6.0 (3) | 6.0 (1) | 6.0 (2) | 6.0 (3) |
| Deodorant | | | 0.1 (2) | 0.1 (3) | 0.1 (1) | 0.1 (2) |
| Perfume | 0.5 | 0.5 | 0.5 | 0.5 | 0.5 | 0.5 |
| Protecting and alleviating agent 1 | | | | | | 2.0 |
| Protecting and alleviating agent 2 | | | | | | 1.0 |
| Protecting and alleviating agent 3 | | | | | | 3.0 |

Legend:
Unit: % by weight, W = Water phase, O = Oil phase
Solvent = Purified water
Sequestering agent: Disodium EDTA
Antioxidant: 1 = Ascorbic acid, 2 = Sodium sulfite
Color developer: 1 = Toluene-2,5-diamine sulfate, 2 = 2,4-Diaminophenoxyethanol hydrochloride, 3 = m-Aminophenol, 4 = Resorcinol
Base material: 1 = Cetearyl alcohol, 2 = Behenyl alcohol, 3 = Polyoxyethylene octyl ether phosphate, 4 = Polyoxyethylene oleyl ether phosphate, 5 = Polyoxyethylene cetyl ether phosphate, 6 = Polyoxyethylene stearyl ether phosphate, 7 = Polyoxyethylene cetyl ether (surfactant), 8 = Mineral oil
Alkalizing agent: 1 = Ammonia water (25%), 2 = Monoethanolamine
Deodorant = L-menthol
Perfume = Combined perfume
Protecting and alleviating agent: 1 = Coffee extract , 2 = Milk extract, 3 = Soybean extract
The numbers in parentheses in the contents of alkalizing agent and deodorant in Examples 8 to 11 indicate the mixing order of these components

TABLE 2

| Function | Parts | Example 1 |
|---|---|---|
| Solvent (purified water) | W | Remainder |
| Sequestering agent (disodium EDTA) | W | |
| pH adjusting agent (phosphoric acid) | W | |
| pH adjusting agent (tetrasodium pyrophosphate) | W | |
| Stabilizer (phenacetin) | W | |
| Base material (polyoxyethylene oleyl ether phosphate) | W | |
| Base material (cetearyl alcohol) | W | |
| Oxidizing agent (hydrogen peroxide water (35%)) | W | |

Legend:
Unit: % by weight,
W = Water phase,
O = Oil phase
The second agent applies equally to all Examples of the first agent.

In other words, the same second agent is used in Examples 1 to 11 and Comparative Example 1 of the first agent. Accordingly, only the first agent is different and the second agent is the same in Examples 1 to 11 of the present invention. Hence, Examples and Comparative Example are thus described by the numbers of Examples and Comparative Example of the first agent in the following description.

The production process of the first agent is as follows.

First, a color developer and a solvent among the respective components presented in Table 1 are put in a main tank and melted by being heated at a temperature of 80° C. Separately, the oily components of a base material among the components constituting the first agent are melted by being heated to 80° C. and then put in the main tank, and the components are mixed together. Subsequently the mixture is stirred at 3500 rpm for 25 minutes by using a homomixer for first emulsification. The emulsified mixture is cooled to 55° C., ammonia water of an alkalizing agent is added thereto, and the mixture is stirred at 3500 rpm for 7 minutes by using a homomixer for second emulsification. The cooled and emulsified mixture is cooled to 36° C. again, and a deodorant and monoethanolamine of an alkalizing agent are added thereto, and the mixture is stirred at 3500 rpm for 7 minutes by using a homomixer for third emulsification. The mixture emulsified in the cooling step is again cooled to 27° C., and a coffee extract, a milk extract, and a soybean extract which are a hair protecting and scalp irritation alleviating agent, an antioxidant, a sequestering agent, and a perfume are added thereto, and the mixture is stirred at 3500 rpm for 3 minutes in the above temperature range for fourth emulsification.

The production process of the second agent is as follows.

First, the stabilizer and solvent components among the components constituting the second agent in Table 2 are put in a main tank and melted by being heated to a temperature of 80° C. Separately, the components constituting the base material among the components of the second agent are melted by being heated to a temperature of 80° C. and then put in the main tank, and the components are mixed together. Subsequently, the mixture is stirred at 3500 rpm for 7 minutes by using a homomixer for emulsification. The emulsified mixture is cooled to 35° C., the sequestering agent, the pH adjusting agent, and the oxidizing agent are then added thereto, and the mixture is stirred at 3500 rpm for 3 minutes for emulsification, thereby completing the operation.

EXPERIMENTAL EXAMPLE 1

Figure 4:
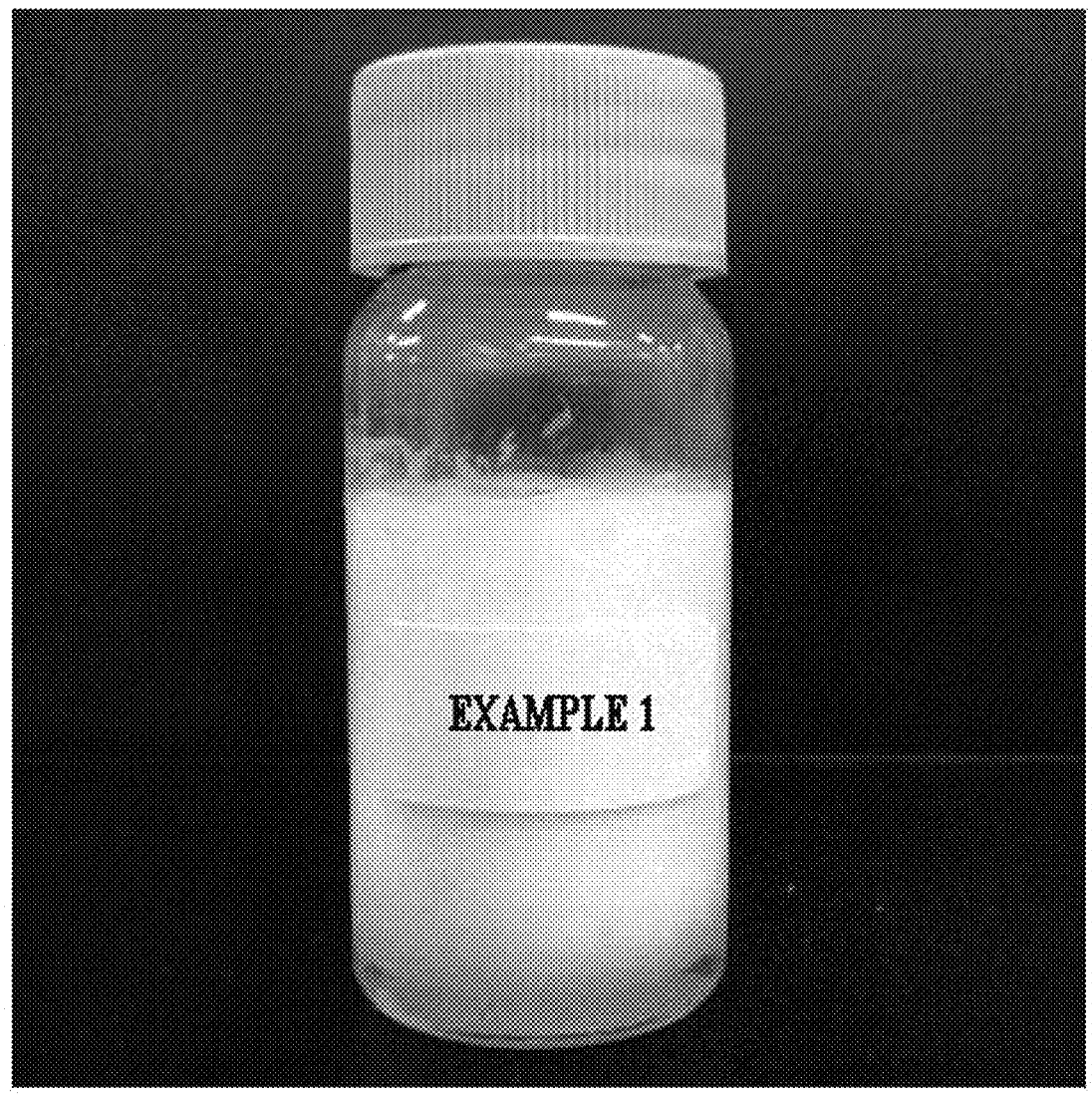
FIG. 4 and FIG. 5 are photographs illustrating results of experiments on the stability of layered micelle structure of polyoxyethylene octyl ether phosphate and polyoxyethylene oleyl ether phosphate among the base materials used in the present invention.
Figure 5:
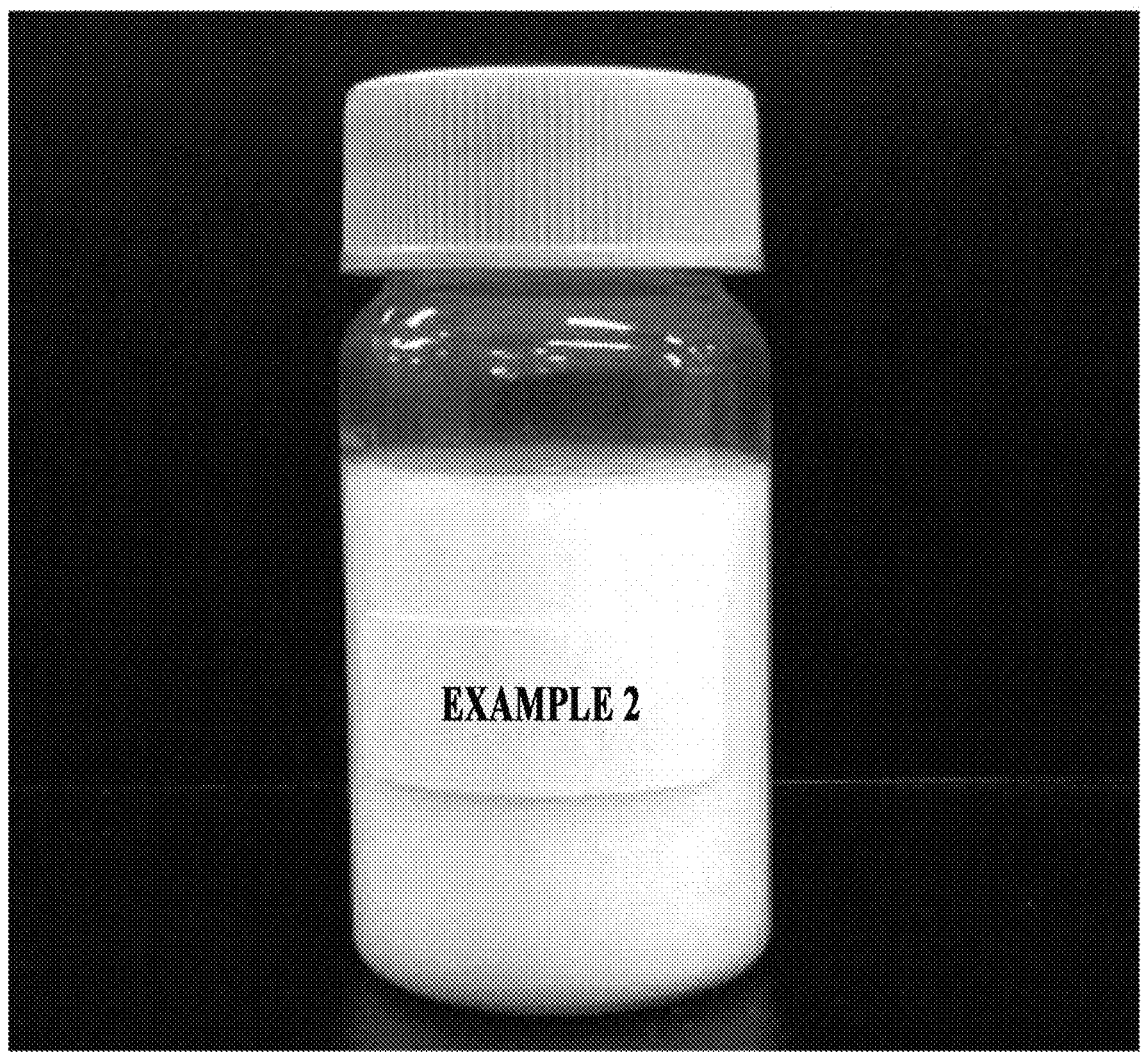

The experiment on the stability of polyoxyethylene octyl ether phosphate and polyoxyethylene oleyl ether phosphate has been conducted. The experiment on the stability of the layered micelle structure of polyoxyethylene octyl ether phosphate and polyoxyethylene oleyl ether phosphate among the base materials has been conducted, and as a result of test at 50° C. for 30 days, the most favorable stability is exhibited in Example 7 containing polyoxyethylene octyl ether phosphate and polyoxyethylene oleyl ether phosphate at a ratio of 1:2. From this, it has been confirmed that the most stable layered micelle structure is formed when the ratio of polyoxyethylene octyl ether phosphate to polyoxyethylene oleyl ether phosphate is 1:2 (see FIGS. 4 and 5). In FIG. 4, which is a photograph of Example 1 according to the present invention, a transparent color portion is observed at the bottom. This indicates that the high temperature stability is relatively lower as compared to FIG. 5, which is a photograph of Example 2, and a slight separation phenomenon has occurred in Example 1.

Particularly, Example 1 exhibits a favorable effect of decreasing ammonia odor as it forms a layered structure, but it is slightly inferior in the long-term stability. Example 2 exhibits excellent effect of decreasing ammonia odor as it forms a layered structure and it exhibits excellent long-term stability as well. Examples 3 and 4 exhibit favorable stability but do not exhibit a high effect of decreasing ammonia odor as they have failed to form a stable layered structure. Example 5 exhibits favorable stability but the effect of decreasing ammonia odor time dependently decreases as the layer structure formed by the phosphate-based substances is collapsed by the influence of a compound (polyoxyethylene cetyl ether) capable of functioning as a surfactant.

EXPERIMENTAL EXAMPLE 2

The sensory evaluation of the deodorizing effect depending on the order of addition of ammonia water, L-menthol, and monoethanolamine among the components added was carried out. A questionnaire survey to examine the effect of decreasing ammonia odor in the hair-dyes of Examples 8, 9, and 10 has been conducted to 80 selected subjects in an age group of from 20 to 50 years old. A general hair-dye of the present company is used as Comparative Example 1. Specifically, the IMON HAIR COLOR CREAM 13 (a styling product turning to a greatly bright light golden color) manufactured by AreumDawoon Cosmetics Co., Ltd. is used. This product contains ammonia water and monoethanolamine of an alkalizing agent at 9.0% by weight and 6.0% by weight, respectively. The order of addition in this product system is simultaneous, and this product is an existing product having strong ammonia odor.

TABLE 3

| Division | Response | Points (%) | Remarks |
| --- | --- | --- | --- |
| Comparative Example 1 | +++ | 100 | Sensory test result after mixing of first agent and second agent |
| Example 8 | −/+ | 18 | |
| Example 9 | + | 35 | |
| Example 10 | ++ | 65 | |

As presented in Table 3, the decrease rate is most favorable in Example 8. This indicates that the raw material components are stably disposed in layers of the layered micelle structure according to the order of addition thereof so that ammonia water is positioned at the innermost part of the micelle, L-menthol among the raw material components is present in the oil phase layer, and monoethanolamine is present in the outermost water phase layer.

EXPERIMENTAL EXAMPLE 3

Figure 6:
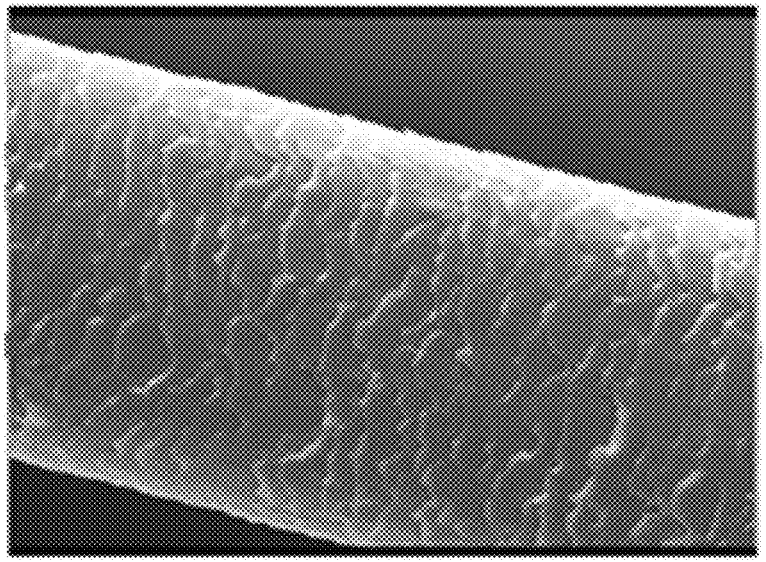
FIG. 6 through FIG. 9 are photographs illustrating an effect of protecting the hair after hair-dyeing, FIG. 6 illustrating the photograph of Comparative Example 1, FIG. 8 illustrating the photograph of Example 8, FIGS. 7 and 9 illustrating the photographs of Example 11.
Figure 7:
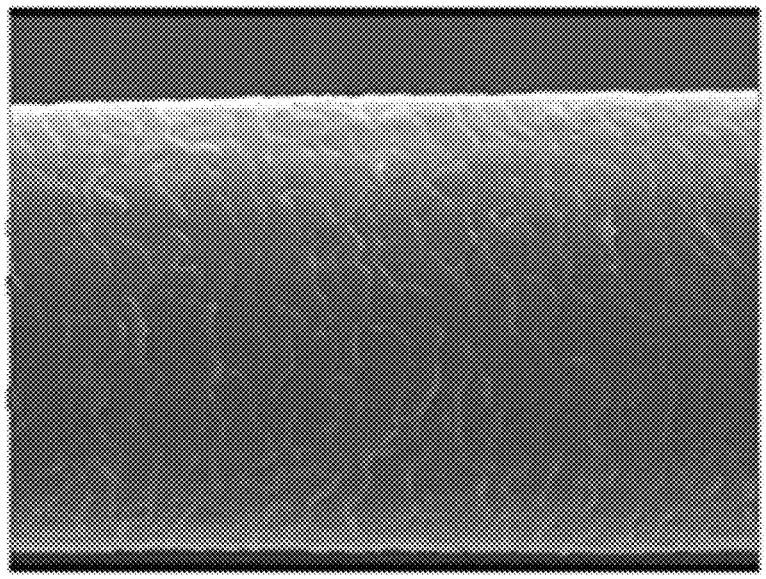
Figure 8:
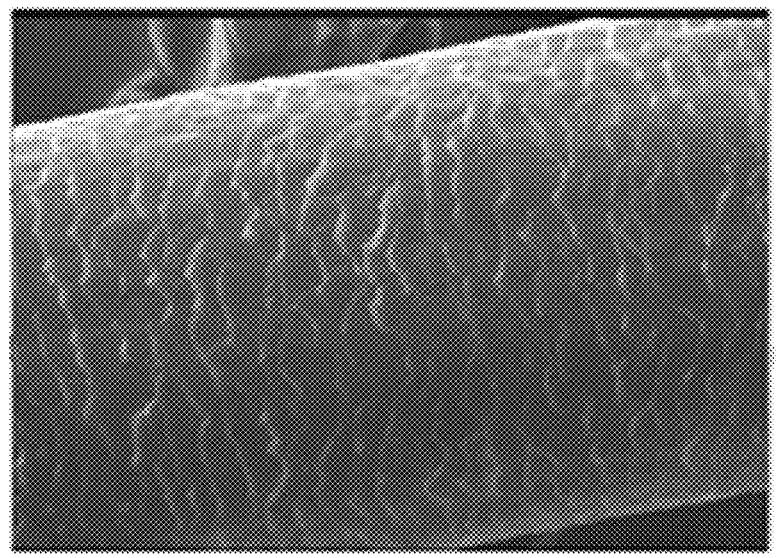
Figure 9:
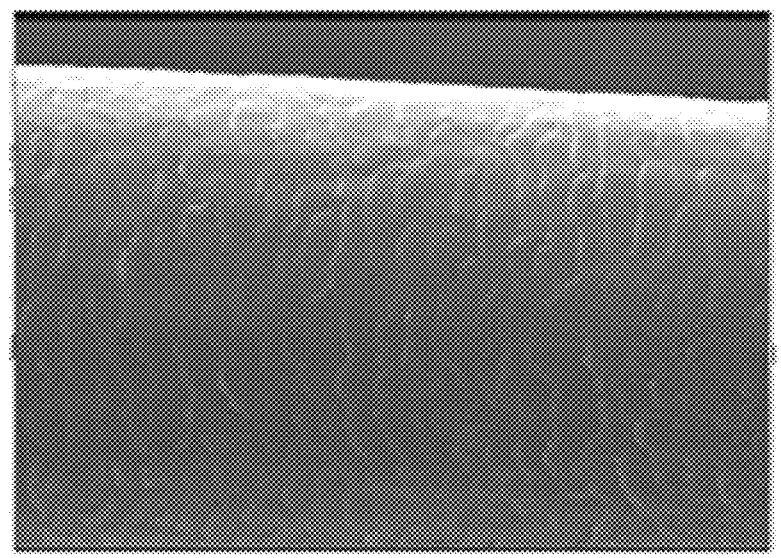

The effect of protecting the hair after hair-dyeing when coffee extract, milk extract, and soybean extract of a scalp protecting and irritation alleviating agent among the components added are added at a ratio of 2:1:3 has been examined by taking a photograph. FIG. 6 illustrates the photograph of Comparative Example 1, FIG. 8 illustrates the photograph of Example 8, FIGS. 7 and 9 illustrate the photographs of Example 11. When FIG. 6 and FIG. 8 are compared to each other, it can be said that the cuticle damage can be slightly decreased as lifting of the hair cuticle is less when a hair-dyeing composition has a layered micelle structure as compared to Comparative Example 1. FIGS. 7 and 9 illustrate the photographs of the hair-dyeing composition of Example 11, and a remarkable effect of protecting the hair cuticle has been observed.

EXPERIMENTAL EXAMPLE 4

The experiment to examine the scalp protecting effect (sensory test on erythema, pruritus, scalp trouble, burning sensation, and the like) has been conducted by using the hair-dyeing composition of Example 11 and selecting the same panels as in Experimental Example 2, and the results are presented in the following Table 4.

TABLE 4

| Scalp protecting effect | Number of panels (persons) | |
| --- | --- | --- |
| Superior | 42 | None |
| Excellent | 28 | Almost none |
| Minor | 8 | Few |

EXPERIMENTAL EXAMPLE 5

Comparative Example 1 and Examples 7, 8, and 11 have been produced, and the hair-dyeing compositions are formed by mixing the first agent and the second agent together and subjected to the dyeing experiment. The dyeing fastness has been determined by immersing the dyed hair in an acidic solution and an alkaline solution which are similar to the sweat components for 48 hours, and visually observing the degree of discoloration, and recording the results. The acidic and alkaline solutions similar to the sweat components have different pH values from each other and have been used to test the sweat fastness. The acidic solution similar to the sweat components is a solution which contains sodium chloride at 10 g/L, lactic acid at 1 g/L, and disodium phosphate (dodecahydrate) 2.5 g and has a pH of 4.5. The alkaline solution similar to the sweat components is a solution which contains sodium chloride at 10 g/L, ammonium carbonate at 4 g/L, and disodium phosphate (dodecahydrate) 2.5 g and has a pH of 8.7.

TABLE 5

| Division | Comparative Example 1 | Example 7 | Example 8 | Example 11 | Remarks |
|---|---|---|---|---|---|
| Dyeing and fastness | Favorable | Favorable | Favorable | Superior | |

Figure 10:
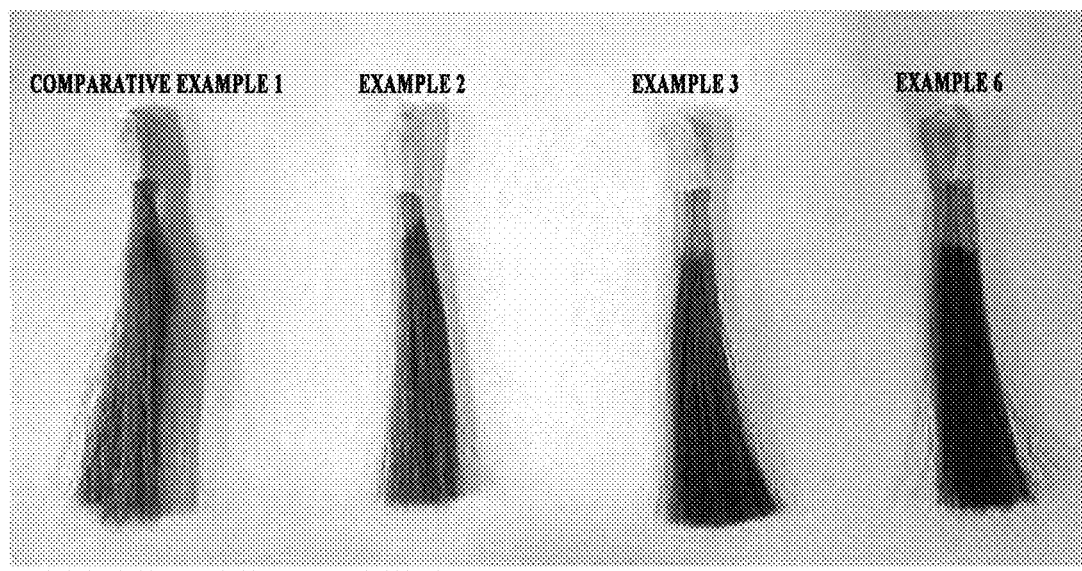
FIG. 10 is a photograph illustrating a hair-dyeing effect.

As presented in Table 5 and FIG. 10, it has been confirmed that the hair-dyeing composition of Example 11 according to the present invention exhibits remarkably superior dyeing property and dyeing fastness to the other compositions.

According to the present invention, it is possible to provide a hair-dyeing composition which is capable of decreasing ammonia odor generated during hair dyeing, especially during hair dyeing using an oxidative hair-dyeing composition, without enhancing or deteriorating the dyeing power and at the same time decreasing damage of the hair and harmfulness to the human body of the hair-dyeing practitioner (hairdresser) and the customer and a method of producing the same.

While the present invention has been described with respect to the specific embodiments, it will be apparent to those skilled in the art that various changes and modifications may be made without departing from the spirit and scope of the invention as defined in the following claims.

What is claimed is:

1. A hair-dyeing composition, comprising:
a first agent that comprises, based on total weight of the first agent:
from 5 to 30% by weight of a base material containing polyoxyethylene octyl ether phosphate and polyoxyethylene oleyl ether phosphate as essential components and additionally an auxiliary component selected from the group consisting of cetearyl alcohol, behenyl alcohol, mineral oil, and any mixture of two or more of these;
from 5 to 25% by weight of an alkalizing agent selected from the group consisting of monoethanolamine, ammonia water having an ammonia concentration of 28% by weight, and any mixture of these;
from 0.01 to 2% by weight of a color developer; and
a remainder that is a solvent; and a second agent that comprises, based on total weight of the second agent:
from 1 to 10% by weight of a base material selected from the group consisting of polyoxyethylene oleyl ether phosphate, cetearyl alcohol, and any mixture of these;
from 12 to 20% by weight of an oxidizing agent;
from 0.1 to 1% by weight of a pH adjusting agent; and
a remainder that is a solvent.

2. The hair-dyeing composition as claimed in claim 1, wherein the first agent further comprises from 0.01 to 0.5% by weight of a deodorant.

3. The hair-dyeing composition as claimed in claim 2, wherein the deodorant is L-menthol.

4. The hair-dyeing composition as claimed in claim 1, wherein the first agent further comprises from 0.1 to 10% by weight of a hair protecting and scalp irritation alleviating agent selected from the group consisting of a coffee extract, a milk extract, a soybean extract, and any mixture of two or more thereof.

5. The hair-dyeing composition as claimed in claim 4, wherein the hair protecting and scalp irritation alleviating agent comprises a mixture of the coffee extract, the milk extract, and the soybean extract that has a mixing ratio by weight of the coffee extract: the milk extract: the soybean extract that is 2:1:3.

* * * * *